United States Patent
Hehle et al.

(10) Patent No.: US 10,890,120 B2
(45) Date of Patent: Jan. 12, 2021

(54) METHOD FOR PRODUCING A FUEL COMPOSITION AND FOR OPERATING AN INTERNAL COMBUSTION ENGINE

(71) Applicant: MTU FRIEDRICHSHAFEN GMBH, Friedrichshafen (DE)

(72) Inventors: Marc Hehle, Constance (DE); Philipp Klaas, Friedrichshafen (DE)

(73) Assignee: MTU FRIEDRICHSHAFEN GMBH, Friedrichshafen (DE)

(*) Notice: Subject to any disclaimer, the term of this patent is extended or adjusted under 35 U.S.C. 154(b) by 463 days.

(21) Appl. No.: 15/751,345

(22) PCT Filed: Jul. 27, 2016

(86) PCT No.: PCT/EP2016/001298
§ 371 (c)(1),
(2) Date: Feb. 8, 2018

(87) PCT Pub. No.: WO2017/028943
PCT Pub. Date: Feb. 23, 2017

(65) Prior Publication Data
US 2018/0230915 A1    Aug. 16, 2018

(30) Foreign Application Priority Data
Aug. 20, 2015   (DE) .................. 10 2015 215 939

(51) Int. Cl.
*C10L 3/00* (2006.01)
*F02D 19/06* (2006.01)
(Continued)

(52) U.S. Cl.
CPC ............ *F02D 19/0671* (2013.01); *C01B 3/34* (2013.01); *C07C 41/01* (2013.01); *C10K 3/06* (2013.01);
(Continued)

(58) Field of Classification Search
CPC .. F02D 19/082; F02D 19/085; F02D 19/0647; F02D 19/0671; F02B 7/06;
(Continued)

(56) References Cited

U.S. PATENT DOCUMENTS 4,408,572 A * 10/1983 Yoon .................. F02B 1/02
123/179.8
4,876,989 A * 10/1989 Karpuk .................. F02B 1/02
123/3
(Continued)

FOREIGN PATENT DOCUMENTS

DE     102012017718 A1    3/2014
EP         0801225 A1    10/1997
(Continued)

*Primary Examiner* — Phutthiwat Wongwian
*Assistant Examiner* — Arnold Castro
(74) *Attorney, Agent, or Firm* — Lucas & Mercanti, LLP; Klaus P. Stoffel

(57) ABSTRACT

A method for producing a fuel composition, including the following steps: providing special gas containing combustible substances; reforming a first part of the special gas by producing synthesis gas; producing dimethyl ether from the synthesis gas by producing a reaction mixture containing a dimethyl ether; separating methanol from the reaction mixture and producing a methanol-reduced dimethyl ether mixture; and bringing together a second part of the special gas with the methanol reduced dimethyl ether mixture in order to obtain the fuel composition.

11 Claims, 1 Drawing Sheet

(51) Int. Cl.
*C10L 3/06* (2006.01)
*F02D 19/08* (2006.01)
*C10K 3/06* (2006.01)
*C10L 1/185* (2006.01)
*C01B 3/34* (2006.01)
*C07C 41/01* (2006.01)
*F02B 7/06* (2006.01)

(52) U.S. Cl.
CPC .............. *C10L 1/1852* (2013.01); *C10L 3/003* (2013.01); *C10L 3/06* (2013.01); *F02B 7/06* (2013.01); *F02D 19/0647* (2013.01); *F02D 19/082* (2013.01); *F02D 19/085* (2013.01); *C01B 2203/0205* (2013.01); *C01B 2203/0475* (2013.01); *C01B 2203/06* (2013.01); *C10L 2270/02* (2013.01); *C10L 2290/02* (2013.01); *C10L 2290/04* (2013.01); *C10L 2290/24* (2013.01); *C10L 2290/54* (2013.01); *Y02T 10/30* (2013.01)

(58) Field of Classification Search
CPC . C10K 3/06; C10L 1/1852; C10L 3/06; C10L 3/003; C10L 2290/02; C10L 2290/04; C10L 2270/02; C10L 2290/24; C10L 2290/54; C01B 3/34; C01B 2203/06; C01B 2203/0205; C01B 2203/0475; C07C 41/01; Y02T 10/36
See application file for complete search history.

(56) References Cited

U.S. PATENT DOCUMENTS

| | | | |
|---|---|---|---|
| 6,205,957 B1 | 3/2001 | Saylor | |
| 6,739,125 B1* | 5/2004 | Mulligan | F01N 3/2073 123/1 A |
| 7,159,541 B2* | 1/2007 | Wakao | C01B 3/38 123/3 |
| 7,449,034 B1* | 11/2008 | Mikkelsen | C10L 1/026 123/1 A |
| 7,614,385 B2* | 11/2009 | Bysveen | F02D 19/0647 123/456 |
| 9,133,779 B2* | 9/2015 | Hughes | F02D 19/0647 |
| 9,140,180 B2* | 9/2015 | Gruber | F02B 43/10 |
| 9,261,053 B2* | 2/2016 | Jacob | F02M 26/36 |
| 10,590,866 B2* | 3/2020 | Magnusson | F02D 19/0647 |
| 2004/0049982 A1* | 3/2004 | Shimizu | C01B 3/501 48/61 |
| 2004/0248999 A1* | 12/2004 | Briscoe | F25J 3/0257 518/703 |
| 2004/0256116 A1* | 12/2004 | Olsvik | C01B 3/34 166/401 |
| 2005/0161017 A1* | 7/2005 | Warlick | F02D 41/0027 123/275 |
| 2009/0123801 A1* | 5/2009 | Yamamoto | C01B 3/323 429/425 |
| 2010/0000153 A1* | 1/2010 | Kurkjian | C01B 3/32 48/127.3 |
| 2013/0025188 A1* | 1/2013 | Cheiky | C05F 9/04 44/307 |
| 2015/0052813 A1* | 2/2015 | Neves | C01B 3/02 48/198.1 |
| 2015/0075471 A1* | 3/2015 | Morris | F02D 19/081 123/1 A |
| 2016/0097349 A1* | 4/2016 | Tokumaru | F02M 21/0212 123/445 |
| 2016/0152537 A1* | 6/2016 | Zubrin | C07C 29/1518 568/698 |
| 2016/0152899 A1* | 6/2016 | Fleckner | C07C 29/1518 518/704 |
| 2016/0245244 A1* | 8/2016 | Katsura | F02M 21/0245 |
| 2016/0251218 A1* | 9/2016 | Cheiky | C01B 3/501 422/148 |
| 2017/0314511 A1* | 11/2017 | Yudanov | F17C 5/02 |
| 2018/0002264 A1* | 1/2018 | Wright | B01J 8/1854 |
| 2019/0048808 A1* | 2/2019 | Lundgren | F02M 37/04 |
| 2019/0127650 A1* | 5/2019 | Boehman | C10L 1/026 |
| 2019/0348699 A1* | 11/2019 | Reytier | H01M 8/04089 |
| 2020/0080519 A1* | 3/2020 | Leidefeldt | F02M 21/06 |

FOREIGN PATENT DOCUMENTS

| | | |
|---|---|---|
| JP | H11293263 A | 10/1999 |
| WO | 2010120965 A1 | 10/2010 |

* cited by examiner

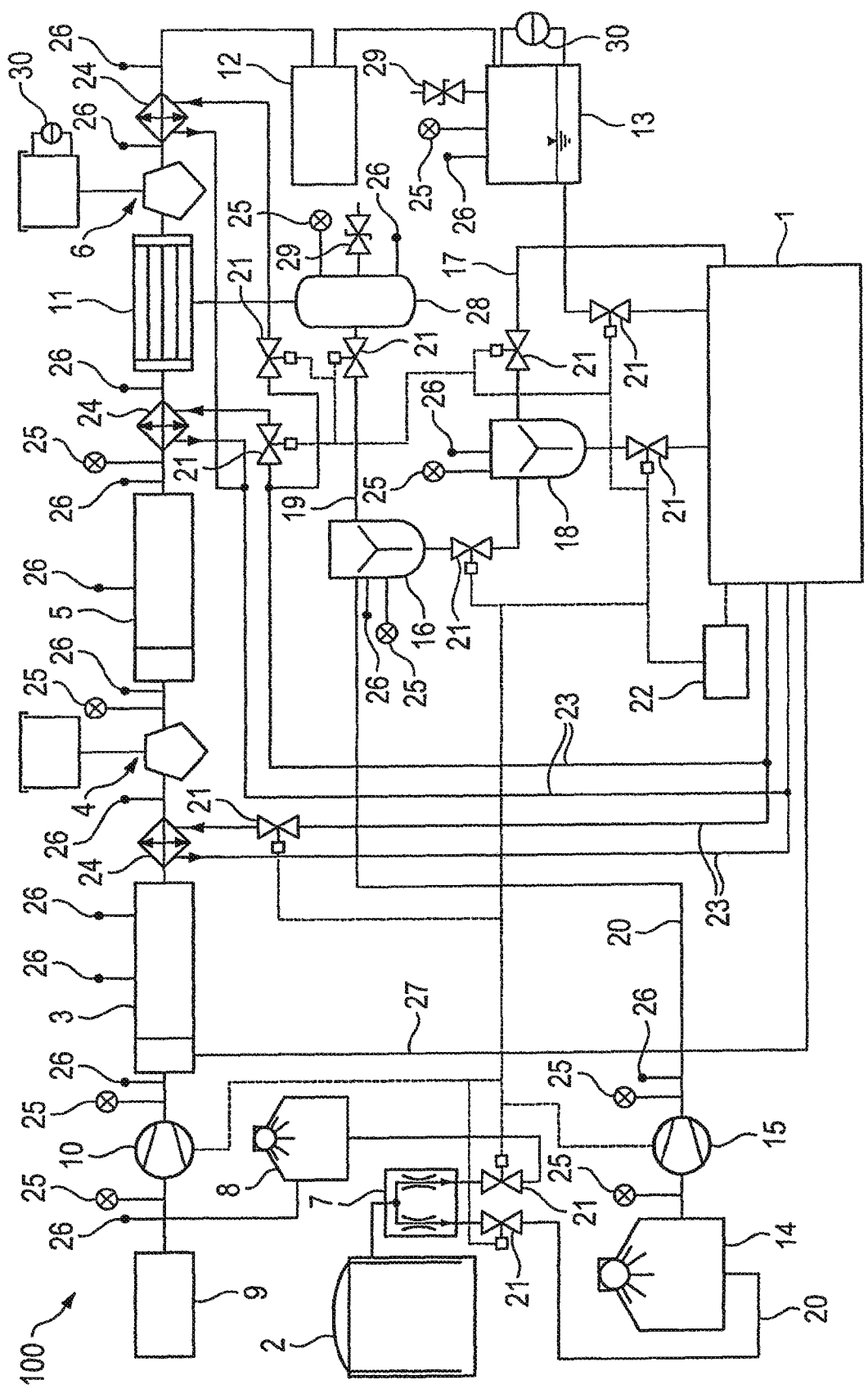

METHOD FOR PRODUCING A FUEL COMPOSITION AND FOR OPERATING AN INTERNAL COMBUSTION ENGINE

The present application is a 371 of International application PCT/EP2016/001298, filed Jul. 27, 2016, which claims priority of DE 10 2015 215 939.6, flied Aug. 20, 2015, the priority of these applications is hereby claimed and these applications are incorporated herein by reference.

BACKGROUND OF THE INVENTION

The invention relates to a method for producing an inexpensive fuel composition. Moreover, the invention also relates to a method for operating an internal combustion engine. According to the invention, the use of reduced-methanol dimethyl ether is also described.

The performance of internal combustion engines essentially depends on the energy content and composition of the fuel mixture used. Synthesis gases produced e.g. by reforming that contain a high content of ignitable hydrogen are therefore used. The production of synthesis gas is a complex and costly process. Synthesis gas can be produced from special gas by purification and subsequent reforming. Special gases, also referred to as lean gases, are as a rule waste gases, which are generated e.g. in gas extraction or in biological or chemical processes and are ordinarily burned at the flare stack or released into the environment without any selective and therefore costly purification. Because of the sensitivity of internal combustion engines and the technical adaptation of the engine to the various special gases connected therewith, use of special gas as a combustion gas has only been possible to date to a highly limited extent.

SUMMARY OF THE INVENTION

The object of the invention is to provide a method for producing a fuel composition in which an ignitable fuel mixture is inexpensively produced that offers high performance and is as consistent as possible with respect to its combustion properties and in which special gas is recovered as combustion gas. A further object of the present invention is to provide a method for operating an internal combustion engine that allows the use of different special gases without technical adaptation of the internal combustion engine and thus allows inexpensive and thus efficient operation of the internal combustion engine. Moreover, another object of the present invention is to provide a use of reduced-methanol dimethyl ether (DME).

This object is achieved by means of the features of the independent claims.

Accordingly, the object is achieved by a method for producing a fuel composition that comprises use with simultaneous partial processing of special gas containing combustible substances. According to the invention, special gas is first produced which, as mentioned above, contains substances that can be converted in a combustion process. In this case, suitable special gases include waste gases and associated gases from the chemical industry and raw material production (e.g. from refining), wood gas, converted gas, pyrolysis gas, firedamp and mine gas, coke-oven gas, landfill gas, biogas, sewage gas, natural gas, flare gas, shale gas, city gas, propane, butane, associated gases generated in steel and iron production (such as cupola furnace gas, top gas, etc.) and mixtures of said gases. Special gases can therefore be of differing origin and composition and accordingly also show differing heat values. More particularly, special gases suitable for the invention can have heat values of less than 1 kWh/$m^3_N$ to >30 kWh/$m^3_N$. The special gas is divided into two partial streams. A first part of the special gas is reformed to synthesis gas by means of a reforming method or by combining different methods. As is customary, reforming takes place at high temperatures and optionally under air supply. The synthesis gas obtained comprises substances such as hydrogen ($H_2$), carbon monoxide (CO), carbon dioxide ($CO_2$), nitrogen ($N_2$), water and optionally residues of longer-chain hydrocarbons from the special gases that could not be reformed. Dimethyl ether (DME) is produced from the synthesis gas obtained. For example, dimethyl ether can be obtained from the synthesis gas by distillation. Alternatively, dimethyl ether can also be synthesized. In the process of producing dimethyl ether (e.g. using a copper/zinc oxide/aluminum oxide catalyst), methanol is generated, among other substances. The synthesis of dimethyl ether can therefore advantageously be carried out by catalytic conversion of methanol, with maintenance of corresponding boundary conditions (pressure, temperature) and subsequent dehydration. In the production of dimethyl ether, a DME-containing reaction mixture is produced that can contain DME and further reaction products, such as e.g. methanol and residual synthesis gas. Methanol is then separated from the dimethyl ether-containing reaction mixture, resulting in the production of a reduced-methanol dimethyl ether mixture. It has been found that methanol alters the ignitability and combustion properties of DME and thus the combustion of special gases. Depending on the methanol content, a DME-containing reaction mixture that contains methanol and is supplied for combustion shows reduced and fluctuating combustion properties, which prevents the combustion of special gas having stable high efficiency. The separation of methanol from the mixture, leading to production of essentially methanol-free DME, is therefore advantageous. The residual methanol content of the reduced-methanol dimethyl ether mixture should preferably not exceed 50 vol %, and is more preferably less than 10 vol %. The reduced-methanol dimethyl ether mixture can be stored prior to completion of the fuel composition, for example in a tank or storage receptacle. Preferably, any further reaction products can be separated from the reaction mixture in order to obtain DME that is as pure as possible. The reduced-methanol dimethyl ether mixture is then brought together with a second part of the special gas to obtain the fuel composition. After this, the fuel composition is preferably immediately used for the production of energy. This bringing together can take place directly in a combustion chamber of an internal combustion engine or in a separate container such as a storage tank, or in an area upstream of a combustion chamber. In the fuel composition produced according to the invention, because of its favorable auto-inflammability, DME is preferably used in the combustion process as an ignition jet that initiates and maintains the combustion of unreformed special gas. Because of the stable ignition and combustion properties of the reduced-methanol dimethyl ether mixture produced from the synthesis gas, special gases of differing compositions can be reliably ignited, which provides flexibility in special gas selection. The method according to the invention thus allows simple and inexpensive recovery of special gas of any kind. Special gas, which is ordinarily discarded as waste gas, can therefore be sustainably reused without requiring complex purification of the entire special gas stream.

The dependent claims comprise advantageous improvements and embodiments of the invention.

In an advantageous improvement of the method according to the invention, it is provided that $CO_2$ is separated from the synthesis gas produced by reforming, in particular immediately after reforming. This improves the ignitability of the dimethyl ether-containing reaction mixture.

Moreover, bringing together of the second part of the special gas with the reduced-methanol dimethyl ether mixture is advantageously carried out in a combustion chamber of an internal combustion engine. In this way, the dimethyl ether can be used as an ignition jet in combustion of the special gas, and for example can be added for this purpose during each compression of the fuel composition.

Furthermore, in order to improve the ignitability of the fuel composition, synthesis gas can advantageously be added to the fuel composition. In this case, the synthesis gas can originate from external sources or from synthesis gas obtained by reforming. Preferably, the synthesis gas is removed after reforming and before DME production, as this promotes complete recovery of the synthesis gases and thus the sustainability of the method according to the invention.

Provided that the fuel composition already shows high ignitability or low knock resistance, its waste gas, which is obtained by combustion of the fuel composition, can advantageously be added to the fuel composition.

By means of advantageous selective or variable addition of synthesis gas and waste gas to the fuel composition, the combustion characteristics of the fuel composition can be controlled and unified so that combustion of the widest range of special gases can be carried out without changing the hard- and software components involved in combustion of the special gases.

Moreover, a method for operating an internal combustion engine is further described according to the invention. The method comprises the steps of i) provision of special gas, ii) production of synthesis gas by reforming a first part of the special gas, iii) production of dimethyl ether from the synthesis gas by producing a reaction mixture containing a dimethyl ether, iv) separation of methanol from the dimethyl ether-containing reaction mixture and production of a reduced-methanol dimethyl ether mixture, v) supplying of a second part of the special gas and the reduced-methanol dimethyl ether mixture to a combustion chamber of the internal combustion engine and vi) ignition of the second part of the special gas by igniting the reduced-methanol dimethyl ether mixture. Here, method steps i) through iv) are identical to the corresponding method steps of the method according to the invention for the production of a fuel composition. The actual combustion of the fuel composition takes place in method step iv), wherein for this purpose, the special gas and a reduced-methanol DME mixture are fed into a combustion chamber in method step v) and then ignited with the production of pressure and burned. The dimethyl ether contained in the reduced-methanol dimethyl ether mixture serves as a self-igniting component, preferably as an ignition jet, for igniting the second part of the special gas. The ignition of the DME than also causes ignition of the special gas. Because of the stable high ignitability of the DME that is achieved by separation of methanol and the accompanying use of the reduced-methanol DME mixture, the method according to the invention allows the efficient provision of energy from special gases containing different combustible substances without first requiring complex purification or specific adaptation of the internal combustion engine to the respective special gases to be used. In this way, special gases with heat values of less than 1 kWh/m³$_N$ to >30 kWh/m³$_N$ can be converted according to the invention. As special gases can thus be obtained at little or no cost, the operation of an internal combustion engine according to the invention is also flexible, cost-efficient, and at the same time, because of the use of waste gas, sustainable.

The ignitability of the dimethyl ether-containing reaction mixture can be improved by means of the advantageous step of separating $CO_2$ from the synthesis gas produced by reforming, which is carried out more particularly immediately after reforming.

In order to further improve the ignitability of the special gas, an improvement of the method according to the invention provides a step of feeding synthesis gas into the combustion chamber.

The synthesis gas is advantageously mixed with the second part of the special gas before being fed into the combustion chamber.

In order to reduce the ignitability of the special gas, waste gas from the internal combustion engine can advantageously be fed into the combustion chamber.

By means of suitable variable feeding of synthesis gas and waste gas into the combustion chamber, the combustion properties of the special gas can be controlled and unified, which is beneficial for the stable combustion of differing special gases.

A further advantageous embodiment provides that the combustion chamber comprises a prechamber and a main chamber. Preferably, the reduced-methanol dimethyl ether mixture is ignited in the prechamber, and in this process, the resulting flames are guided into the main chamber, where extremely rapid combustion of the second part of the special gas can take place.

The reduced-methanol dimethyl ether mixture is advantageously stored in a tank until it is used. In this manner, for example, it is possible in the method for operating an internal combustion engine to react more quickly and flexibly to corresponding power requirements. If more power is required, a larger amount of special gas is used, and a correspondingly larger amount of DME is fed in and ignited. In addition, it is possible to more easily handle temporary requirements and start-up processes.

Moreover, the use of dimethyl ether as an ignition jet for igniting special gas containing combustible substances in a combustion chamber of an internal combustion engine is further described according the invention, wherein the content of methanol in the dimethyl ether is less than 50 vol %, and preferably less than 10 vol %. The reduced-methanol DME, i.e. DME containing less methanol, has stable ignition and combustion properties, so that special gases having differing compositions and containing combustible substances can be efficiently ignited with stable ignition performance.

BRIEF DESCRIPTION OF THE DRAWING

Further details, advantages, and features of the present invention are given in the follow description of an example with reference to the drawing. The drawing is as follows:

FIG. 1 is a flow chart illustrating the method for operating an internal combustion engine according to an advantageous embodiment of the invention.

DETAILED DESCRIPTION OF THE INVENTION

Only the essential aspects of the advantageous embodiment are shown in FIG. 1. All other aspects have been omitted for purposes of clarity.

FIG. 1 shows the essential devices of a system 100 that is suitable for operating an internal combustion engine according to an advantageous improvement of the method. These devices comprise an internal combustion engine 1, a special gas source 2, a reformer 3, a $CO_2$ separator 4, a DME production device 5 and a methanol separator 6. Combustible substances containing special gas are first prepared from the special gas source 2. In this case, suitable special gases include waste gases and associated gases from the chemical industry and raw material production (e.g. from refining), wood gas, converted gas, pyrolysis gas, firedamp and mine gas, coke-oven gas, landfill gas, biogas, sewage gas, natural gas, flare gas, shale gas, city gas, propane, butane, associated gases generated in steel and iron production (such as cupola furnace gas, top gas, etc.), and mixtures of said gases. The special gas is fed through a flow divider 7 that separates the special gas into a first part and a second part. The first part of the special gas is supplied to a gas washing unit 8, and depending on the reforming process used, the washed special gas is optionally compressed together with air from an air supply device 9 in a compressor 10 and then supplied to the reformer 3. In the reformer 3, the special gas is reformed and synthesis gas is obtained. For this purpose, the reformer 3 can be supplied via the power line 27 with power produced in the internal combustion engine 1. The synthesis gas obtained comprises substances such as hydrogen ($H_2$), carbon monoxide (CO), carbon dioxide ($CO_2$), water, and residue of special gas components, such as longer-chain hydrocarbons in particular. $CO_2$ is separated from the synthesis gas in the $CO_2$ separator 4 and removed therefrom. The remaining synthesis gas is supplied to the DME production device 5, in which DME is produced from the synthesis gas. In addition to residual unconverted synthesis gas, the dimethyl ether-containing reaction mixture obtained in production also contains DME, methanol and $CO_2$. The dimethyl ether-containing reaction mixture can be fed through a condenser 11 in which any reaction products of DME can be separated. Methanol is then separated from the reaction mixture in the methanol separator 6. The reduced-methanol dimethyl ether mixture can optionally be subjected to post-treatment in a post-treatment unit 12, and for example can be cooled to room temperature and brought to a pressure of approx. 8 bar in order to liquefy the DME. The reduced-methanol dimethyl ether mixture, which after processing can also be pure DME, can be temporarily stored in a tank 13 or immediately supplied to one or more combustion chambers of the internal combustion engine 1. The second part of the special gas can also be supplied via a special gas line 20 to a washing unit 14 and then optionally compressed in a compressor 15. Via a mixing device 16, the optionally washed and compressed special gas can also be fed into one or more combustion chambers of the internal combustion engine 1. In the combustion chamber, gas is burned with accompanying generation of pressure. Here, the DME serves as an ignition jet for the special gas to be burned, more specifically the second part of the special gas. In other words, the DME, which is auto-ignitable under pressure, is ignited in the reduced-methanol dimethyl ether mixture, subsequently causing the special gas to be ignited and burned. Via an exhaust gas recirculation line 17, waste gas from the internal combustion engine 1 can be mixed for example with the second part of the special gas to be supplied to the internal combustion engine 1, which reduces the ignitability of the special gas. For this purpose, a mixing device 18 is provided in which the waste gas is mixed with the second part of the special gas before being fed into the combustion chamber. Via a synthesis gas line 19, synthesis gas remaining from production of the DME-containing reaction mixture, which is separated in the condenser 11 and optionally stored in a synthesis gas storage unit 28, can be supplied to the second part of the special gas, and for example can also be fed into the mixing device 16. In this manner, the ignitability of the second part of the special gas can be increased. This makes it possible to adapt and control the ignitability of the fuel composition depending on the energy content, knocking tendency and ignitability of the special gases used. In the individual lines of the system 100 for operating an internal combustion engine, valves 21 are provided that allow or block substance transport and are controlled and regulated by mans of a control and regulation device 22. In order to improve the energy efficiency of the system 100, heat exchange can advantageously be carried out between hot and cold areas of the system 100. The heat exchange can take place via heat lines 23 and heat exchangers 24. Where necessary, pressure measurement points 25, temperature measurement points 26, pressure relief valves 29 and level indicators 30 can be present in the system 100. By feeding special gas and reduced-methanol DME into the internal combustion engine 1, special gas of any desired composition can be efficiently used with stable combustion performance and ignition power to provide energy in the internal combustion engine 1 without requiring specific adaptation of the internal combustion engine 1 to the respective special gas to be used.

In addition to the above written description of the invention, for supplementary disclosure thereof, specific reference is made to the drawing of the invention in FIG. 1.

The invention claimed is:

1. A method for producing a fuel composition, comprising the steps of:
   providing special gas containing combustible substances, the special gas being selected from the group consisting of: waste gas, associated gas from chemical industry or raw material production, wood gas, converted gas, pyrolysis gas, firedamp or mine gas, coke-oven gas, landfill gas, biogas, sewage gas, natural gas, flare gas, shale gas, city gas, propane, butane, associated gases generated in steel and iron production, and mixtures of said gases;
   producing synthesis gas by reforming a first part of the special gas;
   producing dimethyl ether from the synthesis gas by producing a reaction mixture containing a dimethyl ether;
   separating methanol from the reaction mixture and producing a reduced-methanol dimethyl ether mixture; and
   controlling and standardizing combustion properties of the fuel composition by a variable addition of synthesis gas and waste gas obtained by combustion of the fuel composition to said fuel composition; and
   bringing together a second part of the special gas with the reduced-methanol dimethyl ether mixture to obtain the fuel composition.

2. The method according to claim 1, further comprising separating $CO_2$ from the synthesis gas produced by reforming.

3. The method according to claim 2, including separating $CO_2$ from the synthesis gas immediately after reforming.

4. The method according to claim 1, wherein the steps of bringing together the second part of the special gas with the reduced-methanol dimethyl ether mixture is carried out in a combustion chamber of an internal combustion engine.

5. A method for operating an internal combustion engine, comprising the steps of:

providing special gas containing combustible substances, the special gas being selected from the group consisting of: waste gas, associated gas from chemical industry or raw material production, wood gas, converted gas, pyrolysis gas, firedamp or mine gas, coke-oven gas, landfill gas, biogas, sewage gas, natural gas, flare gas, shale gas, city gas, propane, butane, associated gases generated in steel and iron production, and mixtures of said gases;

producing synthesis gas by reforming a first part of the special gas;

producing dimethyl ether from the synthesis gas by producing a reaction mixture containing a dimethyl ether;

separating methanol from the reaction mixture and producing a reduced-methanol dimethyl ether mixture;

supplying of a second part of the special gas and the reduced-methanol dimethyl ether mixture to a combustion chamber of the internal combustion engine;

controlling and standardizing combustion properties of the special gas by a variable feeding of synthesis gas and waste gas of the internal combustion engine into the combustion chamber; and igniting the second part of the special gas by igniting the reduced-methanol dimethyl ether mixture.

6. The method according to claim 5, further comprising separating $CO_2$ from the synthesis gas produced by reforming.

7. The method according to claim 6, including separating $CO_2$ from the synthesis gas immediately after reforming.

8. The method according to claim 5, wherein the combustion chamber comprises a prechamber and a main chamber.

9. The method according to claim 5, further comprising storing the reduced-methanol dimethyl ether mixture in a tank.

10. The method according to claim 5, wherein the dimethyl ether has a methanol content of less than 50%.

11. The method according to claim 10, wherein the methanol content is less than 10 vol %.

* * * * *